(12) United States Patent
Kim (10) Patent No.: US 10,543,026 B2
(45) Date of Patent: Jan. 28, 2020

(54) FRACTURE FIXATION DEVICE HAVING CLIP FOR STABILIZING INTRAMEDULLARY NAIL

(71) Applicant: THE GENERAL HOSPITAL CORPORATION, Boston, MA (US)

(72) Inventor: Saechin Kim, Andover, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/305,223

(22) PCT Filed: Apr. 21, 2015

(86) PCT No.: PCT/US2015/026842
§ 371 (c)(1),
(2) Date: Oct. 19, 2016

(87) PCT Pub. No.: WO2015/164355
PCT Pub. Date: Oct. 29, 2015

(65) Prior Publication Data
US 2017/0042592 A1  Feb. 16, 2017

Related U.S. Application Data

(60) Provisional application No. 61/981,946, filed on Apr. 21, 2014.

(51) Int. Cl.
*A61B 17/70* (2006.01)
*A61B 17/72* (2006.01)
(Continued)

(52) U.S. Cl.
CPC ........ *A61B 17/7233* (2013.01); *A61B 17/744* (2013.01); *A61B 17/746* (2013.01); *A61B 17/8061* (2013.01)

(58) Field of Classification Search
CPC .............. A61B 17/7233; A61B 17/7266
See application file for complete search history.

(56) References Cited

U.S. PATENT DOCUMENTS

| 3,716,050 A | 2/1973 | Johnston |
| 4,915,092 A * | 4/1990 | Firica ............. A61B 17/7208 606/64 |

(Continued)

OTHER PUBLICATIONS

Akilapa, Elastic Stable Intramedullary Nail for Paediatric Femoral Fractures, WebmedCentral Trauma 2012, 3(5): WMC003325, 19 pages.

(Continued)

*Primary Examiner* — Pedro Philogene
*Assistant Examiner* — David C Comstock
(74) *Attorney, Agent, or Firm* — Quarles & Brady LLP (57) ABSTRACT

Fracture fixation devices and methods achieve stabilization of a bone fragment. A nail section of the device is dimensioned to be positioned within an intramedullary canal of a bone such that the nail section spans a fracture site in the bone. The nail section bends into a post-insertion configuration different from a pre-insertion configuration when inserted into the intramedullary canal. The nail fastening section is connected to the nail section by a connecting element on a first side of the fracture site. At least a portion of the nail fastening section is positioned outside the bone. A first end of the nail section and a second end of the nail fastening section are positioned on an opposite second side of the fracture site when the fracture fixation device is implanted in the bone.

27 Claims, 5 Drawing Sheets

(51) Int. Cl.
*A61B 17/74* (2006.01)
*A61B 17/80* (2006.01)

(56) References Cited

U.S. PATENT DOCUMENTS

| | | | |
|---|---|---|---|
| 5,197,966 A | 3/1993 | Sommerkamp | |
| 6,296,645 B1* | 10/2001 | Hover | A61B 17/72 606/62 |
| 6,379,359 B1 | 4/2002 | Dahners | |
| 6,551,321 B1 | 4/2003 | Burkinshaw et al. | |
| 6,730,090 B2 | 5/2004 | Orbay et al. | |
| 7,037,308 B2 | 5/2006 | Medoff | |
| 7,811,286 B2* | 10/2010 | Medoff | A61B 17/68 606/151 |
| 7,896,886 B2 | 3/2011 | Orbay et al. | |
| 7,927,341 B2 | 4/2011 | Orbay et al. | |
| 7,972,336 B2 | 7/2011 | James et al. | |
| 8,100,910 B2 | 1/2012 | Warburton | |
| 8,100,911 B2 | 1/2012 | Yamazaki et al. | |
| 8,460,343 B2* | 6/2013 | Graham | A61B 17/7233 606/280 |
| 8,486,072 B2 | 7/2013 | Haininger | |
| 8,540,714 B2 | 9/2013 | Gordon et al. | |
| 2002/0099379 A1* | 7/2002 | Adam | A61B 17/72 606/67 |
| 2002/0103488 A1* | 8/2002 | Lower | A61B 17/72 606/62 |
| 2005/0182402 A1* | 8/2005 | Hansson | A61B 17/7233 606/64 |
| 2005/0283154 A1* | 12/2005 | Orbay | A61B 17/1728 606/62 |
| 2007/0173834 A1 | 7/2007 | Thakkar | |
| 2007/0288016 A1* | 12/2007 | Halder | A61B 17/7225 606/62 |
| 2008/0125818 A1* | 5/2008 | Sidebotham | A61B 17/72 606/329 |
| 2008/0262497 A1* | 10/2008 | Nijenbanning | A61B 17/744 606/63 |
| 2008/0287950 A1 | 11/2008 | Frigg et al. | |
| 2009/0018542 A1* | 1/2009 | Saravia | A61B 17/7266 606/63 |
| 2009/0171358 A1* | 7/2009 | Chang | A61B 5/417 606/63 |
| 2009/0216232 A1 | 8/2009 | Buford, III et al. | |
| 2010/0211120 A1* | 8/2010 | Bonutti | A61B 17/0401 606/86 R |
| 2010/0305623 A1* | 12/2010 | Klaue | A61B 17/72 606/329 |
| 2010/0331843 A1* | 12/2010 | Grusin | A61B 17/7225 606/64 |
| 2011/0028974 A1* | 2/2011 | Chemello | A61B 17/7216 606/63 |
| 2011/0066152 A1* | 3/2011 | Keller | A61B 17/725 606/62 |
| 2011/0066190 A1* | 3/2011 | Schaller | A61B 17/7266 606/301 |
| 2011/0087227 A1* | 4/2011 | Mazur | A61B 17/68 606/62 |
| 2011/0137312 A1* | 6/2011 | Mantovani | A61B 17/7233 606/63 |
| 2011/0178520 A1* | 7/2011 | Taylor | A61B 17/7208 606/62 |
| 2012/0059428 A1* | 3/2012 | Epperly | A61B 17/7225 606/310 |
| 2013/0012942 A1* | 1/2013 | Nelson | A61B 17/7208 606/63 |
| 2013/0116693 A1* | 5/2013 | Nelson | A61B 17/7233 606/64 |
| 2013/0123785 A1* | 5/2013 | Fonte | A61B 17/72 606/63 |
| 2013/0204250 A1* | 8/2013 | McDevitt | A61B 17/0401 606/64 |
| 2013/0274747 A1* | 10/2013 | Fagan | A61B 17/7266 606/64 |
| 2014/0074093 A9 | 3/2014 | Nelson et al. | |
| 2015/0038968 A1* | 2/2015 | Vega | A61B 17/744 606/64 |
| 2015/0201978 A1* | 7/2015 | Piccin | A61B 17/7208 606/63 |
| 2016/0256202 A1* | 9/2016 | Halder | A61B 17/7266 |

OTHER PUBLICATIONS

Perez, Which Makes the Better Medical Nail: Titanium or Stainless Steel?, Copyright 2004 Penton Media, Inc., 3 pages.

Ramseier, et al., Femoral Fractures in Adolescents: A Comparison of Four Methods of Fixation, J Bone Joint Surg Am., 2010, 92:1122-1129.

Synthes, The Titanium Elastic Nail System, Technique Guide, Copyright 1998 Synthes (USA), 32 pages.

Wall, et al., Complications of Titanium and Stainless Steel Elastic Nail Fixation of Pediatric Femoral Fractures, J Bone Joint Surg Am., 2008, 90:1305-1313.

PCT International Search Report and Written Opinion, PCT/US2015/026842, dated Jul. 16, 2015, 13 pages.

* cited by examiner

FRACTURE FIXATION DEVICE HAVING CLIP FOR STABILIZING INTRAMEDULLARY NAIL

CROSS-REFERENCE TO RELATED APPLICATIONS

This application represents the U.S. National Stage of International Application No. PCT/US2015/026842, filed Apr. 21, 2015 which claims priority to U.S. Provisional Patent Application Ser. No. 61/981,946 filed Apr. 21, 2014, both of which are incorporated herein by reference for all purposes.

STATEMENT REGARDING FEDERALLY SPONSORED RESEARCH

Not Applicable.

FIELD OF THE INVENTION

This invention relates to fracture fixation devices and methods.

BACKGROUND OF THE INVENTION

Flexible intramedullary nails are used to stabilize long bone fractures in pediatric patients. They are mostly used in forearm fractures (radius and ulna) as well as humerus, femur, and tibia fractures when casting is not appropriate. The nails work well when the fracture is at the diaphysis (the middle of the bone where the medullary canal is the narrowest—see FIG. 2A) because the tight fit between the nail and the medullary canal promote stability between the two, resulting in stability of the fracture at the diaphysis. Because the nails are inserted through a small incision, they allow minimally invasive surgical treatment of fractures.

However, there are long bone fractures for which the use of flexible intramedullary nails is challenging. For example, when the fracture is at the proximal metaphysis where the medullary canal is wider (see FIG. 2B), creating a tight fit between the nails and the medullary canal at the fracture site is difficult. Without the tight fit, there is no control over the proximal fragment, allowing the proximal fragment to displace (see FIG. 2C).

Therefore, what is needed is fracture fixation devices and methods in which improved stabilization of a bone fragment to an intramedullary nail can be achieved.

SUMMARY OF THE INVENTION

The present disclosure meets the foregoing needs by providing a fracture fixation device including a nail section and a nail fastening section. The nail section is dimensioned to be positioned within an intramedullary canal of a bone such that the nail section spans a fracture site in the bone. Preferably, the nail section has a pre-insertion configuration, and the nail section comprises a flexible material such that when the nail section is inserted in the intramedullary canal, the nail section bends into a post-insertion configuration different from the pre-insertion configuration. When bending into the post-insertion configuration, the nail section creates frictional force at points where the nail section contacts an inner surface of the intramedullary canal. The nail fastening section is connected to the nail section by a connecting element on a first side of the fracture site. At least a portion of the nail fastening section is positioned outside the bone when the fracture fixation device is implanted in the bone. A first end of the nail section and a second end of the nail fastening section are positioned on an opposite second side of the fracture site when the fracture fixation device is implanted in the bone of a subject. When the bone of the subject has a growth plate (as in a pediatric bone), flexibility of the nail section allows the nail section to be inserted at a point in the bone that avoids disruption of the growth plate.

The connecting element can be a bend integrally formed with the nail section and the nail fastening section. The nail section can bend into a generally bowed shaped when the nail section is inserted into the intramedullary canal.

The nail fastening section can include a first throughhole for receiving a first bone screw and a second throughhole for receiving a second bone screw. The first throughhole may be located on the first side of the fracture site when the fracture fixation device is implanted in the bone, and the second throughhole may be located on the second side of the fracture site when the fracture fixation device is implanted in the bone. The fracture fixation device may further include a first locking screw dimensioned to be inserted into the bone through the first throughhole, and a second locking screw dimensioned to be inserted into the bone through the second throughhole. The first throughhole may be angled such that the first screw avoids the nail section when the first screw is advanced into the bone, and the second throughhole may be angled such that the second screw avoids the nail section when the second screw is advanced into the bone. The first throughhole may be offset from a centerline of the nail fastening section such that the first screw avoids the nail section when the first screw is advanced into the bone, and the second throughhole may be offset from the centerline of the nail fastening section such that the second screw avoids the nail section when the second screw is advanced into the bone.

The connecting element can comprise a tubular section of the nail fastening section. The tubular section may be dimensioned to be placed over the nail section. A set screw can be used for securing the nail section in the tubular section of the nail fastening section. The connecting element may comprise a projection of the nail fastening section, the projection being dimensioned to be placed in a cannula of the nail section.

The nail fastening section can include a concave surface and/or a convex surface dimensioned to match a shape of an outer cortex of the bone. The nail fastening section can have a serpentine shape.

In another embodiment, the fracture fixation device comprises a nail section dimensioned to be positioned within an intramedullary canal of a bone such that the nail section spans a fracture site in the bone; and a separate nail fastener including a nail fastening section and a connecting element for connecting the nail fastener to the nail section. At least a portion of the nail fastening section of the nail fastener is positioned outside the bone when the fracture fixation device is implanted in the bone. A first end of the nail section and a second end of the nail fastening section are positioned on an opposite second side of the fracture site when the fracture fixation device is implanted in the bone.

The connecting element can have a tubular section dimensioned to be placed over the nail section. A set screw can be provided for securing the nail section in the tubular section of the connecting element.

The nail section can have a cannula, and the connecting element may be a projection dimensioned to be inserted in the cannula when the fracture fixation device is implanted in the bone. The projection may be dimensioned to form an interference fit when inserted in the cannula. The nail section can comprise a rigid material.

The nail section may comprise a flexible material such that when the nail section is inserted in the intramedullary canal, the nail section bends into a post-insertion configuration different from the pre-insertion configuration and such that in bending into the post-insertion configuration, the nail section creates frictional force at points where the nail section contacts an inner surface of the intramedullary canal.

The nail fastening section may include a first throughhole for receiving a first bone screw and a second throughhole for receiving a second bone screw. The first throughhole may be located on the first side of the fracture site when the fracture fixation device is implanted in the bone, and the second throughhole may be located on the second side of the fracture site when the fracture fixation device is implanted in the bone. The nail section may include a third throughhole for receiving a third bone screw.

The present disclosure also provides a method for treating a bone fracture in a subject. The method uses one of the fracture fixation devices of the present disclosure. The nail section of the fracture fixation device is positioned within an intramedullary canal of the bone such that the nail section spans a fracture site in the bone; and the nail fastening section is positioned adjacent an outside surface of the bone. When the bone has a growth plate, the nail section is inserted at a point in the bone that avoids disruption of the growth plate. The nail fastening section may include a first throughhole for receiving a first bone screw, and the method may comprise advancing the first bone screw through the first throughhole and into the bone.

In the method, the bone may be a radius, a pediatric radius, an ulna, a pediatric ulna, a humerus, a pediatric humerus, a tibia, a pediatric tibia, a femur, a pediatric femur, or a clavicle.

One concept of this present disclosure is the stabilization of a proximal bone fragment to the flexible intramedullary nail, by using a nail fastener at the proximal end of the nail. As a point of information, standard rigid intramedullary nails are used to stabilize fractures in skeletally mature patients. These intramedullary nails are mostly cannulated; a flexible guide wire is inserted across the fracture site and the nail has a cannula so that the nail can be inserted over the guide wire, across the fracture site. In addition, the nails have perforations proximally and distally so that interlocking screws can be inserted percutaneously to stabilize the bone fragments to the nail. These rigid intramedullary nails should not be used in growing children because they would have to be inserted across the growth plate. Flexible nails are used instead because they can be inserted without crossing the growth plate. But, flexible intramedullary nails do not have a cannula and therefore, there has not been a way to stabilize a fracture fragment to the nail.

Even in adult cases when rigid intramedullary nails are used, there are circumstances when additional proximal stability is desired. For example, in proximal tibia fractures, even when the alignment is acceptable when the nail is inserted, over time the proximal fragment can migrate. Additional proximal fixation would be beneficial in these scenarios.

A fracture fixation device of the present disclosure allows for additional fixation or stabilization between the intramedullary nail and the proximal fracture fragment by using a nail fastener at the proximal end of the nail that is extramedullary and can slide along the outer cortex of the proximal bone. This nail fastener can take the shape of a plate, and may be a part of the nail or a separate implant, and can be used with or without screws that can lock to the plate. Locking screws provide stability by engaging in only the cortex. The locking capability may be a beneficial component because regular screws provide best stability with bicortical purchase which may not always be possible when there is the intramedullary nail that can block the path of the screw.

In one embodiment of a fracture fixation device of the present disclosure, there is provided a redesigned intramedullary nail that looks more like a clip, with one leg comprising a flexible material and a second leg having a concave surface that would match the shape of the outer cortex of the bone. The second leg can function as a fracture fixation plate with or without locking screw capability and can be contoured as needed to match the outer cortex of the bone.

In another embodiment of a fracture fixation device of the present disclosure, a separate nail fastener is used with the flexible intramedullary nail. The nail fastener includes a tubular section that can fit around the intramedullary nail, usually flexible. The nail fastener includes a leg that can slide along the outer cortex of the bone. The leg can be shaped to function as a fracture plate with or without locking screw capability. A set screw can be threaded into the tubular section so that the nail can be stabilized within the tubular section. The nail fastener allows for a combination of intramedullary and extramedullary stabilization of the fracture.

In another embodiment of a fracture fixation device of the present disclosure, a separate nail fastener is used with a standard rigid intramedullary nail. A projection of the nail fastener can be inserted into a cannula of the proximal end of the intramedullary nail in a press fit type of insertion. The leg can slide along the outer cortex of the bone. The leg can be shaped to function as a fracture plate with or without locking screw capability.

A fracture fixation device of the present disclosure can be used in pediatric fractures where flexible intramedullary nails are used. It can be used in long bone fractures that are not short diaphyseal fractures, such as metaphyseal fractures (closer to the joint) of the distal radius, proximal humerus, proximal ulna, and proximal tibia. In young children, femur fractures are often long oblique fractures and have been treated traditionally in a spica cast, which is a whole body cast from the nipple down to the ankle. Intramedullary nails and a nail fastener of the present disclosure would allow for fixation of the fracture with sufficient stability such that a brace can be used rather than a spica cast.

A fracture fixation device of the present disclosure also allows for treatment of certain fractures in adults using flexible intramedullary nails in a minimally invasive way. One example would be in treating clavicle fractures that have been traditionally treated non-operatively. Because shoulder biomechanics have shown poorer function than previously thought, more and more surgeons are recommending surgical treatment. Standard treatment is plating but this requires repeat surgery for plate removal because the plate is prominent and with removal, there is a refracture rate. In addition, a long incision has to be placed over the clavicle. With a flexible intramedullary nail and a nail fastener of the present disclosure, the incision would be small and the nail can be left in place. There are multiple studies that support using flexible nails for clavicle fractures but the concern is that the nail can migrate. Using a nail fastener of the present disclosure would greatly decrease the motion between the nail and the bone that contributes to the migration of the nail. In addition, it would help to maintain fracture reduction. A set screw can be designed into the tubular section of the nail fastener that can be used to prevent the nail from slipping and migrating.

Another example would be minimally invasive treatment of peri-articular fractures such as the distal radius, proximal ulna (olecranon), and proximal humerus in adults. The nail fastener for proximal humerus fracture may have multiple screw holes transversely to allow for multiple fixation points at the same level.

Another example use would be in treating proximal long bone fractures where rigid intramedullary nail fixation is used, such as hip fractures or proximal tibia fractures.

A pre-contoured bone fastener of the present disclosure with one leg in the intramedullary canal and other leg outside, sliding along the bone would give relatively greater stability than a single rod. Example uses would be in pediatric fractures such as femur, radius, tibia, ulna. It can also be used in the clavicle. The clavicle can be a problem because of fractures after a plate is removed. A pre-contoured bone fastener of the present disclosure can be shaped serpentine for use in the clavicle. Once early callus has formed, the bone fastener can be removed. A pre-contoured bone fastener of the present disclosure can be used in a pediatric femur, which often has long spiral/oblique fractures. Conventional flexible nails will not give support in this case. However, a bone fastener of the present disclosure would give enough support so that perhaps a spica cast can be avoided. The bone fastener of the present disclosure can be supplemented by the usual flexible nail or a second bone fastener but there is a need to avoid neurovascular bundle.

The term "subject" as used herein means an animal. In certain versions of the devices and methods of the present disclosure, the subject is a mammal, preferably a human. Thus, the devices and methods of the present disclosure have applications in veterinary medicine and human medicine.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following detailed description.

DETAILED DESCRIPTION OF THE INVENTION

Figure 1:
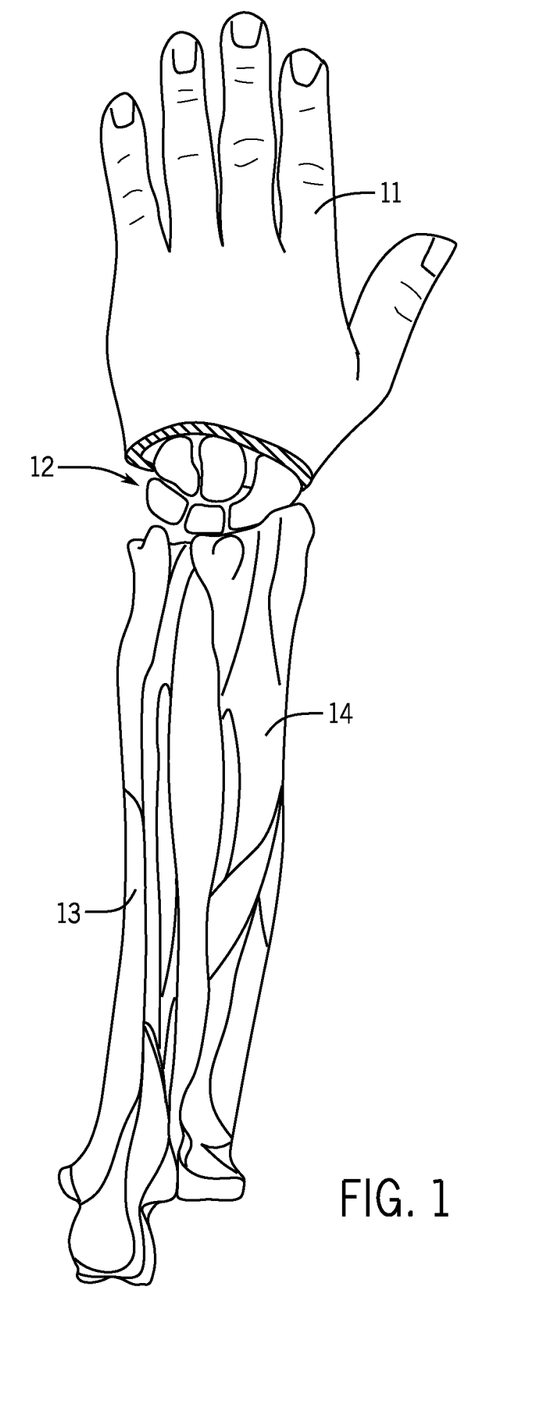
FIG. 1 is a posterior view of the human hand showing carpal bones, the ulna, and the radius.
Figures 2A, 2B:
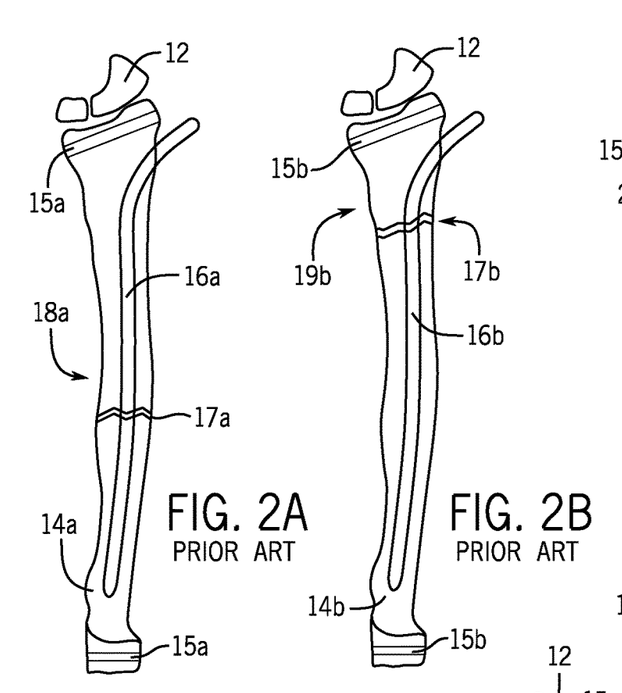
FIG. 2A is a posterior view of the radius of FIG. 1 wherein a flexible intramedullary nail has been used to treat a fracture at the diaphysis.
FIG. 2B is a posterior view of the radius of FIG. 1 wherein a flexible intramedullary nail has been used to treat a fracture at the metaphysis.
Figure 2C:
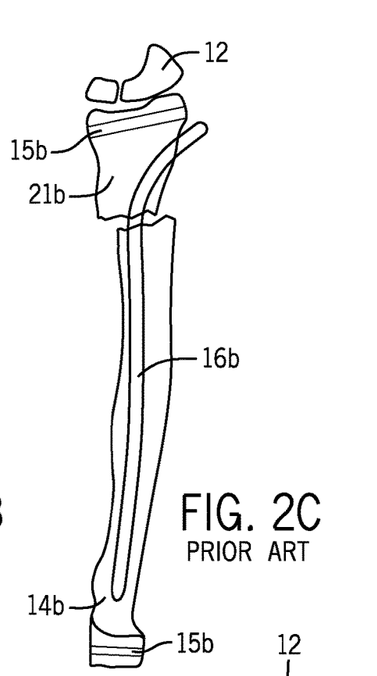
FIG. 2C is a posterior view of the treated radius of FIG. 2B wherein displacement has occurred at the fracture site.

FIGS. 1 to 2C show prior methods for treating fractures in the distal human radius. FIG. 1 shows a human hand 11, carpal bones 12, the ulna 13, and the radius 14. FIG. 2A shows a pediatric radius 14a with growth plates 15a wherein a flexible intramedullary nail 16a has been used to treat a fracture 17a at the diaphysis 18a. FIG. 2B shows a pediatric radius 14b with growth plates 15b wherein a flexible intramedullary nail 16b has been used to treat a fracture 17b at the metaphysis 19b. FIG. 2C is a view of the treated radius 14b of FIG. 2B wherein displacement has occurred at the fracture site. Without a tight fit between the intramedullary canal and the intramedullary nail 16b, there is no control over the proximal fragment 21b, allowing the proximal fragment 21b to displace left in the view of FIG. 2C.

Figures 3, 4:
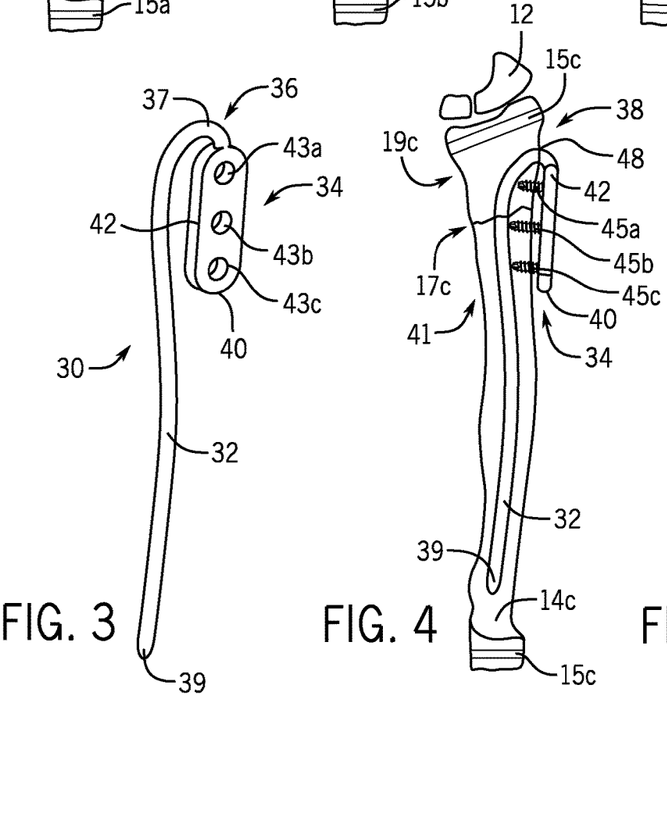
FIG. 3 is a perspective view of an example embodiment of a fracture fixation device of the present disclosure.
FIG. 4 is a posterior view of the radius of FIG. 1 wherein a fracture fixation device of FIG. 3 has been used to treat a fracture at the metaphysis.
Figure 5:
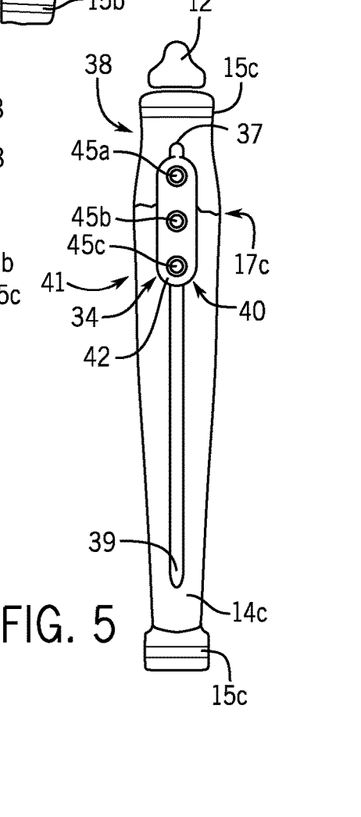
FIG. 5 is a lateral view of the radius of FIG. 1 wherein a fracture fixation device of FIG. 3 has been used to treat a fracture at the metaphysis.

Turning now to FIGS. 3-5, there is shown an example embodiment of a fracture fixation device 30 of the present invention. The fracture fixation device 30 includes a nail section 32 dimensioned to be positioned within an intramedullary canal of a bone such as the pediatric radius 14c shown in FIGS. 4 and 5. The nail section 32 spans a fracture site 17c at the metaphysis 19c of the pediatric radius 14c.

The nail section 32 is flexible and therefore, if the curvature of the nail section 32 is different from that of the medullary canal into which the nail section 32 will be inserted, the nail section 32 acts like a spring in bending to obtain fixation. The nail section 32, when placed down an intramedullary canal, bends and in doing so creates frictional force at the points where it contacts the inner surface of the intramedullary canal. The nail section 32 has a working length defined as the length of the nail section 32 that spans the fracture site 17c between medullary wall contact areas. Because the nail section 32 is flexible, the nail section 32 has a pre-insertion configuration and a post-insertion configuration different from the pre-insertion configuration. When the nail section 32 is inserted in the intramedullary canal, the nail section 32 bends from the pre-insertion configuration into the post-insertion configuration. In bending into the post-insertion configuration, the nail section 32 creates frictional force at points where the nail section 32 contacts an inner surface of the intramedullary canal. The flexibility of the nail section 32 allows the nail section 32 to be inserted at a point 48 in the pediatric radius 14c that avoids disruption of the growth plates 15c.

The nail section 32 may bend into a generally bowed shaped when the nail section 32 is inserted into the intramedullary canal. In one example form, the nail section 32 may have diameters such as 2.0, 2.5, 3.0, 3.5, or 4.0 millimeters, and may comprise a titanium alloy (e.g., titanium—6% aluminum—7% niobium) or a stainless steel alloy, or a superelastic nickel-titanium alloy.

The fracture fixation device 30 includes a nail fastening section 34 connected to the nail section 32 by a connecting element 36 on a first side 38 of the fracture site 17c. The connecting element 36 in the embodiment of FIGS. 3-5 is a bend 37 integrally formed with the nail section 32 and the nail fastening section 34. As shown in FIGS. 4 and 5, at least a portion of the nail fastening section 34 is positioned outside the pediatric radius 14c when the fracture fixation device 30 is implanted in the pediatric radius 14c. A first end 39 of the nail section 32 and a second end 40 of the nail fastening section 34 are dimensioned to be positioned on an opposite second side 41 of the fracture site 17c when the fracture fixation device is implanted in the pediatric radius 14c.

In the embodiment of the fracture fixation device 30 in FIGS. 3-5, the nail fastening section 34 is in the form of an oblong plate 42 with curved opposite ends. The plate 42 includes three throughholes 43a, 43b, 43c for receiving three bone screws 45a, 45b, 45c, respectively. Throughhole 43a is located in the plate 42 such that the throughhole 43a is on the first side 38 of the fracture site 17c when the fracture fixation device 30 is implanted in the pediatric radius 14c. Throughholes 43b, 43c are located in the plate 42 such that the throughholes 43b, 43c are located on the second side 41 of the fracture site 17c when the fracture fixation device 30 is implanted in the pediatric radius 14c. Any number of the bone screws 45a, 45b, 45c may be unicortical locking screws with an externally threaded head that engages and locks into internal threads of the throughholes 43a, 43b, 43c. An axis of any number of the throughholes 43a, 43b, 43c may be angled obliquely with respect to a surface of the plate 42 such that the bone screws 45a, 45b, 45c avoid the nail section 32 when the bone screws 45a, 45b, 45c are advanced into the pediatric radius 14c.

The fracture fixation device 30 can be implanted in the pediatric radius 14c as follows. A drill bit or awl is used to create an entry opening at the point 48 in the pediatric radius 14c that avoids disruption of the growth plates 15c. The surgeon advances the drill bit or awl until it reaches the medullary canal. Using fluoroscopy, the first end 39 of the nail section 32 (which may be bowed in the pre-insertion configuration) is aligned so that it will glance off the far cortex. The nail section 32 is advanced through the drilled entry hole such that the first end 39 of the nail section 32 is glancing off the far cortex and is advancing. The flexible nail section 32 will bend as it progresses up the medullary canal. The nail section 32 is advanced past the fracture site 17c to a position such as shown in FIG. 4. The bone screws 45a, 45b, 45c are then advanced into the pediatric radius 14c through the throughholes 43a, 43b, 43c. Once callus has formed, the fracture fixation device 30 may be removed.

Figures 6, 7, 8:
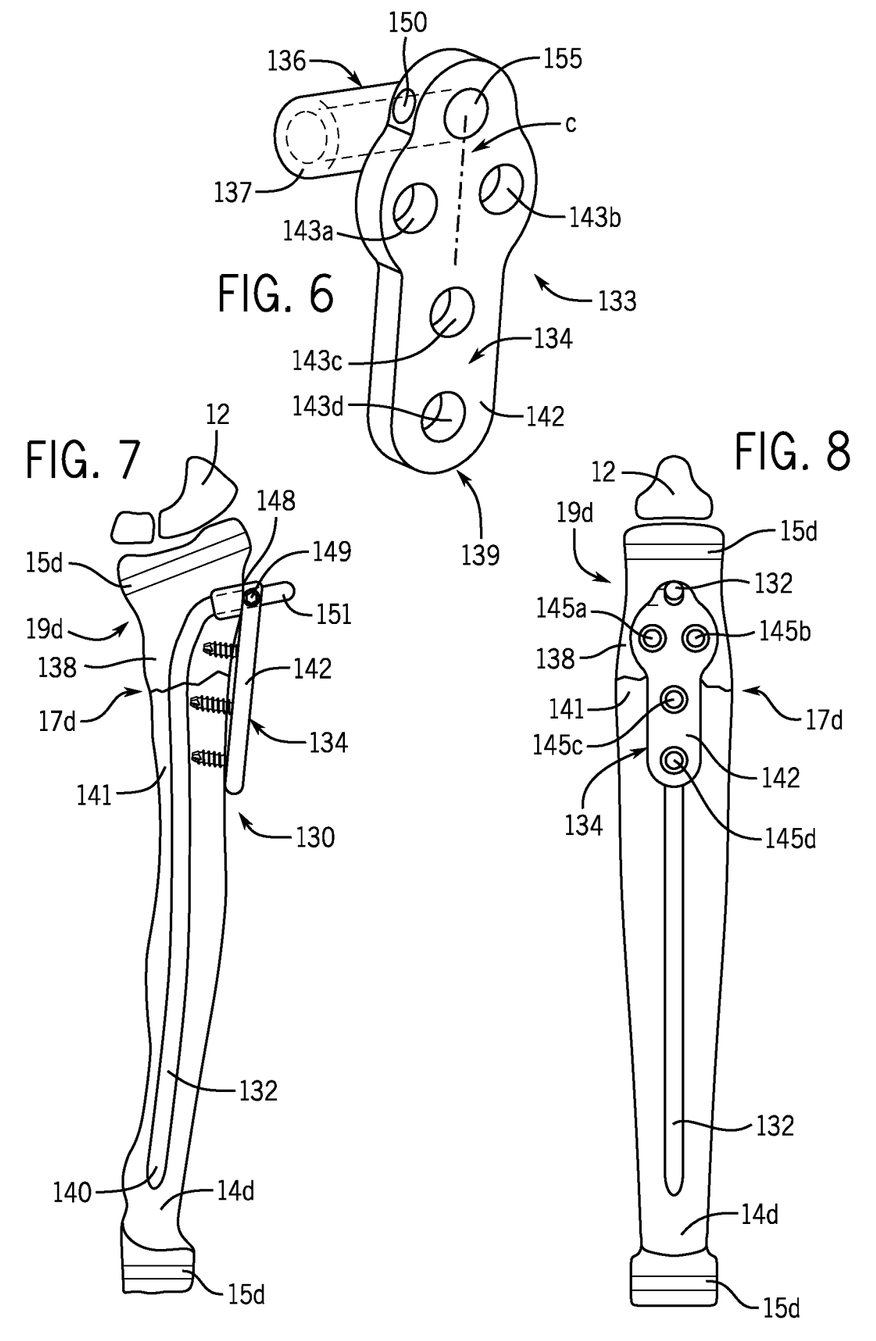
FIG. 6 is a perspective view of a nail fastener of another example embodiment of a fracture fixation device of the present disclosure.
FIG. 7 is a posterior view of the radius of FIG. 1 wherein a fracture fixation device of FIG. 6 has been used to treat a fracture at the metaphysis.
FIG. 8 is a lateral view of the radius of FIG. 1 wherein a fracture fixation device of FIG. 6 has been used to treat a fracture at the metaphysis.

Turning now to FIGS. 6-8, there is shown an example embodiment of another fracture fixation device 130 of the present invention. The fracture fixation device 130 includes a nail section 132 dimensioned to be positioned within an intramedullary canal of a bone such as the pediatric radius 14d shown in FIGS. 7 and 8. The nail section 132 is dimensioned to span a fracture site 17d at the metaphysis 19d of the pediatric radius 14d.

The nail section 132 is flexible and therefore, if the curvature of the nail section 132 is different from that of the medullary canal into which it will be inserted, the nail section 132 acts like a spring in bending to obtain fixation. The nail section 132, when placed down an intramedullary canal, bends and in doing so creates frictional force at the points where it contacts the inner surface of the intramedullary canal. The nail section 132 has a working length defined as the length of the nail section 132 that spans the fracture site 17d between medullary wall contact areas. Because the nail section 132 is flexible, the nail section 132 has a pre-insertion configuration and a post-insertion configuration different from the pre-insertion configuration. When the nail section is inserted in the intramedullary canal, the nail section 132 bends from the pre-insertion configuration into the post-insertion configuration. In bending into the post-insertion configuration, the nail section 132 creates frictional force at points where the nail section 132 contacts an inner surface of the intramedullary canal. The flexibility of the nail section 132 allows the nail section 132 to be inserted at a point 143 in the pediatric radius 14d that avoids disruption of the growth plates 15d. The nail section 132 may bend into a generally bowed shaped when the nail section 132 is inserted into the intramedullary canal. In one example form, the nail section 132 may have diameters such as 2.0, 2.5, 3.0, 3.5, or 4.0 millimeters, and may comprise a titanium alloy (e.g., titanium—6% aluminum—7% niobium), a stainless steel alloy, or a superelastic nickel-titanium alloy.

The fracture fixation device 130 includes a separate nail fastener 133 having nail fastening section 134 connected to the nail section 132 by a connecting element 136 on a first side 138 of the fracture site 17d. The connecting element 136 in the embodiment of FIGS. 6-8 is a cylindrical tubular section 137 integrally formed with the nail fastener 133. As shown in FIGS. 7 and 8, at least a portion of the nail fastener 133 is positioned outside the pediatric radius 14d when the fracture fixation device 130 is implanted in the pediatric radius 14c. The nail section 132 and the nail fastener 133 are dimensioned such that a first end 140 of the nail section 132 and a second end 139 of the nail fastener 133 are positioned on an opposite second side 141 of the fracture site 17d when the fracture fixation device is implanted in the pediatric radius 14d.

In the embodiment of the fracture fixation device 130 in FIGS. 6-8, the nail fastener 133 has a plate section 142 including four throughholes 143a, 143b, 143c, 143d for receiving four bone screws 145a, 145b, 145c, 145d, respectively. Throughholes 143a,143b are arranged in the plate section 142 such that throughholes 143a,143b are located on the first side 138 of the fracture site 17d when the fracture fixation device 130 is implanted in the pediatric radius 14d. The throughholes 145c, 145d are arranged in the plate section 142 such that throughholes 145c, 145d are located on the second side 141 of the fracture site 17d when the fracture fixation device 130 is implanted in the pediatric radius 14d. Any number of the bone screws 145a, 145b, 145c, 145d may be locking screws with an externally threaded head that engages and locks into internal threads of the throughholes 143a, 143b, 143c, 143d. An axis of any number of the throughholes 143a, 143b, 143c, 143d may be angled obliquely with respect to a surface of the plate section 142 such that the bone screws 145a, 145b, 145c, 145d avoid the nail section 132 when the bone screws 145a, 145b, 145c, 145d are advanced into the pediatric radius 14d. The throughhole 143a is offset from a centerline C of the plate section 142 such that the screw 145a can avoid the nail section 132 when a long screw is advanced into the pediatric radius 14d, and the throughhole 143b is offset from the centerline C of the plate section 142 such that a long screw 145b avoids the nail section 132 when the screw 145b is advanced into the pediatric radius 14d.

The fracture fixation device 130 can be implanted in the pediatric radius 14d as follows. A drill bit or awl is used to create an entry opening at the point 148 in the pediatric radius 14d that avoids disruption of the growth plates 15d. The surgeon advances the drill bit or awl until it reaches the medullary canal. Using fluoroscopy, the first end 140 of the nail section 132 (which may be bowed in the pre-insertion configuration) is aligned so that it will glance off the far cortex. The nail section 132 is advanced through the drilled entry hole such that the first end 140 of the nail section 132 is glancing off the far cortex and is advancing. The flexible nail section 132 will bend as it progresses up the medullary canal. The nail section 132 is advanced past the fracture site 17d to a position such as shown in FIG. 7. The central passageway 155 of the tubular section 137 of the nail fastener 133 is then placed over the tip 151 of the nail section 132 (see FIG. 7). A set screw 149 in a threaded opening 150 of the nail fastener 133 can be used to secure the nail fastener 133 to the nail section 132. The bone screws 145a, 145b, 145c, 145d are then advanced into the pediatric radius 14d through the throughholes 145a, 145b, 145c, 145d. The tip 151 of the nail section 132 can be trimmed off using a cutter. Once callus has formed, the fracture fixation device 130 may be removed.

Figure 9:
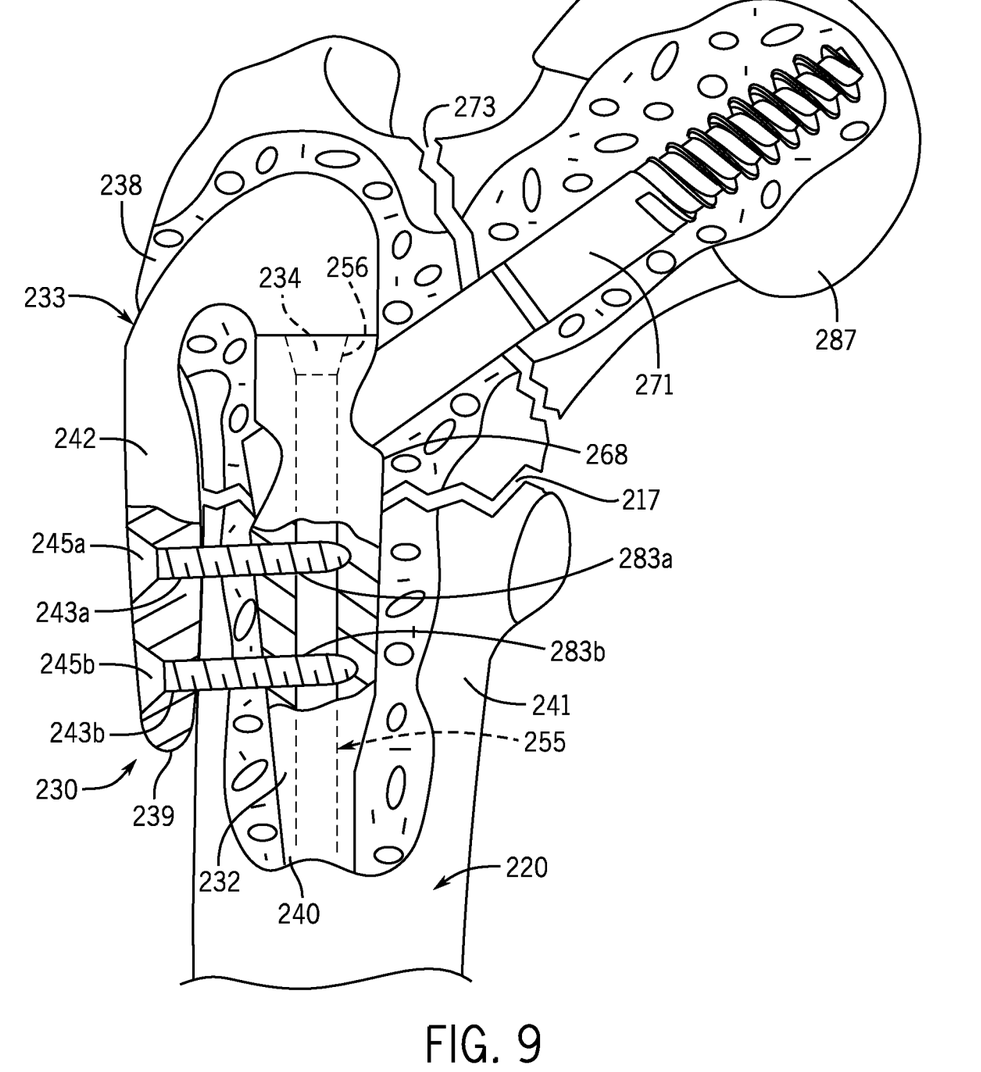
FIG. 9 is an anterior view of a femur wherein another example embodiment of a fracture fixation device of the present disclosure has been used to treat a fracture of the femur.

Turning now to FIG. 9, there is shown an example embodiment of another fracture fixation device 230 of the present invention. The fracture fixation device 230 includes a nail section 232 dimensioned to be positioned within an intramedullary canal of a bone such as the femur 220 shown in FIG. 9. The nail section 232 is dimensioned to span a fracture site 217 in the femur 220.

The nail section 232 is rigid and has a cannula 255 for insertion over a guide wire. The nail section 232 has an opening 268 for receiving a bone screw 271. Because the nail section 232 is rigid, the nail section 232 has identical pre-insertion and post-insertion configurations. The nail section 132 may comprise a titanium alloy, a cobalt chrome alloy, or a stainless steel alloy, or a superelastic nickel-titanium alloy.

The fracture fixation device 230 includes a separate nail fastener 233 having a nail fastening projection 234. The nail fastening projection 234 in the embodiment of FIG. 9 has a frustoconical shape that forms an interference fit when inserted in a countersink 256 at the end of the cannula 255 of the nail section 232. As shown in FIG. 9, at least a portion of the nail fastener 233 is positioned outside the femur 220 when the fracture fixation device 230 is implanted in the femur 220. The nail section 232 is dimensioned such that a first end 240 of the nail section 232 and a second end 239 of the nail fastener 233 are positioned on a second side 241 of the fracture site 217 when the fracture fixation device 230 is implanted in the femur 220.

In the embodiment of the fracture fixation device 230 in FIG. 9, the nail fastener 233 has a plate section 242 including two throughholes 243a, 243b, for receiving two bone screws 245a, 245b, respectively. Throughholes 243a, 243b are arranged in the plate section 242 such that the throughholes 243a, 243b are located on the second side 241 of the fracture site 217 opposite the first side 238 of the fracture site 217 when the fracture fixation device 230 is implanted in the femur 220. Any number of the bone screws 245a, 245b, may be locking screws with an externally threaded head that engages and locks into internal threads of the throughholes 243a, 243b.

The fracture fixation device 230 can be implanted in the femur 220 as follows. The surgeon advances the nail section 232 into the medullary canal past the fracture site 217. The bone screw 271 is advanced through the opening 268 of the nail section 232, past the fracture site 273, and into the head 287 of the femur 220. The projection 234 of the nail fastener 233 is then pressed into the cannula 255 of the nail section 232 creating a press fit to secure the nail fastener 233 to the nail section 232. The bone screws 245a, 245b, are then advanced into the femur 220 through the throughholes 243a, 243b, and into the internally threaded openings 283a, 283b of the nail section 232.

Figures 10, 11, 12:
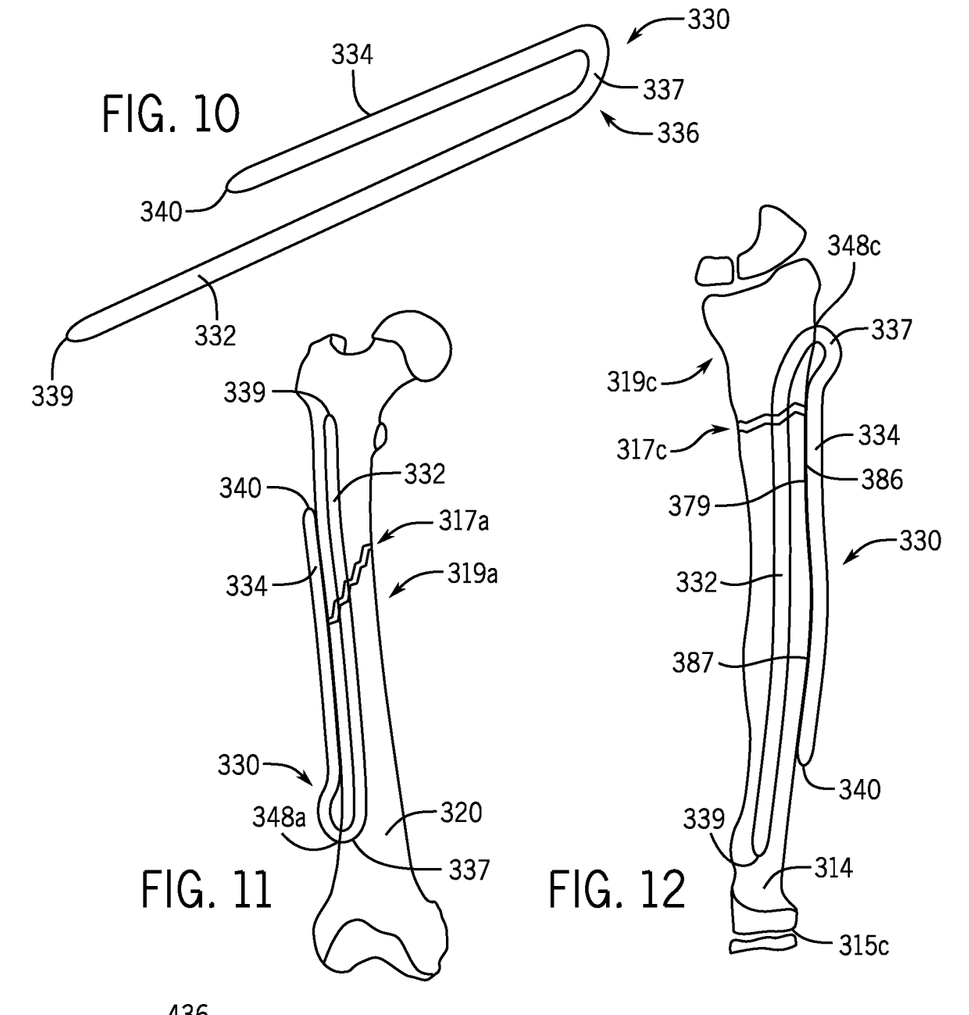
FIG. 10 is a perspective view of another example embodiment of a fracture fixation device of the present disclosure.
FIG. 11 is an anterior view of a femur wherein a fracture fixation device of FIG. 10 has been used to treat a fracture at the diaphysis of a femur.
FIG. 12 is a posterior view of the radius of FIG. 1 wherein another example embodiment of a fracture fixation device has been used to treat a fracture at the metaphysis of a radius.

Referring now to FIGS. 10-12, there is shown an example embodiment of another fracture fixation device 330 of the present invention. The fracture fixation device 330 includes a nail section 332 dimensioned to be positioned within an intramedullary canal of a bone such as the femur 320 of FIG. 11 or the pediatric radius 314 shown in FIG. 12. The nail section 332 is dimensioned to span a fracture site 317a at the diaphysis 319a of the femur 320, or a fracture site 317c at the metaphysis 319c of the pediatric radius 314.

The nail section 332 is flexible and therefore, if the curvature of the nail section 332 is different from that of the medullary canal into which it will be inserted, the nail section 332 acts like a spring in bending to obtain fixation. The nail section 332, when placed down an intramedullary canal, bends and in doing so creates frictional force at the points where it contacts the inner surface of the intramedullary canal. The nail section 332 has a working length defined as the length of the nail section 332 that spans the fracture site 317a or 317c between medullary wall contact areas. Because the nail section 332 is flexible, the nail section 332 has a pre-insertion configuration and a post-insertion configuration different from the pre-insertion configuration. When the nail section is inserted in the intramedullary canal, the nail section 332 bends from the pre-insertion configuration into the post-insertion configuration. In bending into the post-insertion configuration, the nail section 332 creates frictional force at points where the nail section 332 contacts an inner surface of the intramedullary canal. The flexibility of the nail section 332 allows the nail section 332 to be inserted at a point 348a in the femur 320 or a point 348c in the pediatric radius 314 that avoids disruption of the growth plates 315c. The nail section 332 may bend into a generally bowed shaped when the nail section 332 is inserted into the intramedullary canal. In an example form, the nail section 332 may have diameters such as 2.0, 2.5, 3.0, 3.5, or 4.0 millimeters, and the fracture fixation device 330 may comprise a titanium alloy (e.g., titanium—6% aluminum—7% niobium), or a stainless steel alloy, or a superelastic nickel-titanium alloy. Flexibility of the nail section 332 may also be achieved by selective annealing of the nail section 332 after forming the entire fracture fixation device 330 from a rigid material. The selective annealing may leave the sections of the fracture fixation device 330 other than the nail section 332 in a rigid state.

The fracture fixation device 330 includes a nail fastening section 334 connected to the nail section 332 by a connecting element 336. The connecting element 336 in the embodiment of FIGS. 10-12 is a bend 337 integrally formed with the nail section 332 and the nail fastening section 334. As shown in FIGS. 11 and 12, at least a portion of the nail fastening section 334 is positioned outside the femur 320 or the pediatric radius 314 when the fracture fixation device 330 is implanted. The nail section 332 and the nail fastening section 334 are dimensioned such that a first end 339 of the nail section 332 and a second end 340 of the nail fastening section 334 are positioned on the same side of the fracture sites 317a or 317c when the fracture fixation device is implanted in the femur 320 or the pediatric radius 314 as shown in FIGS. 11 and 12. Looking at FIG. 12, the nail fastening section 334 includes a convex surface section 386 that faces the pediatric radius 314 and a concave surface section 387 that faces the pediatric radius 314. The convex surface section 386 and the concave surface section 387 may be structured to match the shape of the outer cortex 379 of the pediatric radius 314.

The fracture fixation device 330 can be implanted in a bone as follows. A drill bit or awl is used to create an entry opening (e.g., at point 348a in FIG. 11 or at point 348c in FIG. 12). The surgeon advances the drill bit or awl until it reaches the medullary canal. Using fluoroscopy, the first end 339 of the nail section 332 (which may be bowed in the pre-insertion configuration) is aligned so that it will glance off the far cortex. The nail section 332 is advanced through the drilled entry hole such that the first end 339 of the nail section 332 is glancing off the far cortex and is advancing. The flexible nail section 332 will bend as it progresses up the medullary canal. The nail section 332 is advanced past the fracture site 317a or 317c to positions such as shown in FIGS. 11 and 12. The nail fastening section 334 includes the convex surface section 386 and the concave surface section 387 dimensioned to match the shape of the outer cortex 379 of the bone such that the nail section 332 is stabilized in the bone. The nail fastening section 334 may be rigid. Once callus has formed, the fracture fixation device 330 may be removed.

Figure 13:
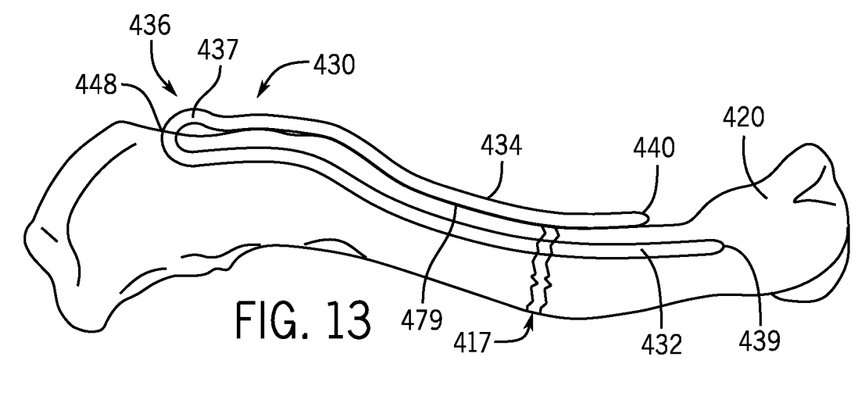
FIG. 13 is a superior view of a right clavicle wherein another example embodiment of a fracture fixation device has been used to treat a fracture of the clavicle.

Looking now at FIG. 13, there is shown an example embodiment of another fracture fixation device 430 of the present invention. The fracture fixation device 430 includes a nail section 432 dimensioned to be positioned within an intramedullary canal of a bone such as the clavicle 420 of FIG. 13. The nail section 432 is dimensioned to span a fracture site 417 of the clavicle 420.

The nail section 432 is flexible and therefore, if the curvature of the nail section 432 is different from that of the medullary canal into which it will be inserted, the nail section 432 acts like a spring in bending to obtain fixation. The nail section 432, when placed down an intramedullary canal, bends and in doing so creates frictional force at the points where it contacts the inner surface of the intramedullary canal. The nail section 432 has a working length defined as the length of the nail section 432 that spans the fracture site 417 between medullary wall contact areas. Because the nail section 432 is flexible, the nail section 432 has a pre-insertion configuration and a post-insertion configuration different from the pre-insertion configuration. When the nail section is inserted in the intramedullary canal, the nail section 432 (which may be bowed in the pre-insertion configuration) bends from the pre-insertion configuration into the post-insertion configuration. In bending into the post-insertion configuration, the nail section 432 creates frictional force at points where the nail section 432 contacts an inner surface of the intramedullary canal. The flexibility of the nail section 432 allows the nail section 432 to be inserted at a point 448 in the clavicle 420. The nail section 432 may bend into a generally bowed shaped when the nail section 432 is inserted into the intramedullary canal. In an example form, the nail section 432 may have diameters such as 2.0, 2.5, 3.0, 3.5, or 4.0 millimeters, and the fracture fixation device 430 may comprise a titanium alloy (e.g., titanium—6% aluminum—7% niobium), or a stainless steel alloy, or a superelastic nickel-titanium alloy. Flexibility of the nail section 432 may also be achieved by selective annealing of the nail section 432 after forming the entire fracture fixation device 430 from a rigid material. The selective annealing may leave the sections of the fracture fixation device 430 other than the nail section 432 in a rigid state.

The fracture fixation device 430 includes a nail fastening section 434 connected to the nail section 432 by a connecting element 436. The connecting element 436 in the embodiment of FIG. 13 is a bend 437 integrally formed with the nail section 432 and the nail fastening section 434. As shown in FIG. 13, at least a portion of the nail fastening section 434 is positioned outside the clavicle 420 when the fracture fixation device 430 is implanted. The nail section 432 and the nail fastening section 434 are dimensioned such that a first end 439 of the nail section 432 and a second end 440 of the nail fastening section 434 are positioned on the same side of the fracture site 417 when the fracture fixation device 430 is implanted in the clavicle 420 as shown in FIG. 13. Looking at FIG. 13, the nail fastening section 434 has a serpentine shape formed by a convex surface section and a concave surface section. The serpentine shape matches the shape of the outer cortex of the clavicle 420 such that the nail section 432 is stabilized in the clavicle 420.

The fracture fixation device 430 can be implanted in the clavicle 420 as follows. A drill bit or awl is used to create an entry opening at point 448 shown in FIG. 13. The surgeon advances the drill bit or awl until it reaches the medullary canal. Using fluoroscopy, the first end 439 of the nail section 432 (which may be bowed in the pre-insertion configuration) is aligned so that it will glance off the far cortex. The nail section 432 is advanced through the drilled entry hole such that the first end 439 of the nail section 432 is glancing off the far cortex and is advancing. The flexible nail section 432 will bend as it progresses up the medullary canal. The nail section 432 is advanced past the fracture site 417 to the position shown in FIG. 13. The nail fastening section 434 the nail fastening section 434 has a serpentine shape dimensioned to match the shape of the outer cortex 479 of the clavicle 420 such that the nail section 432 is stabilized in the clavicle 420. The nail fastening section 434 may be rigid. Once early callus has formed, the fracture fixation device 430 may be removed.

The use of the fracture fixation devices of the present invention in various bones has been described and illustrated herein. The fracture fixation devices can be used beneficially in treating fractures of a radius, an ulna, a pediatric ulna, a humerus, a pediatric humerus, a tibia, a pediatric tibia, a femur, a pediatric femur, and a clavicle. However, these are non-limiting example uses that do not limit use of the fracture fixation devices of the present invention, that is, the fracture fixation devices may be used in other bones.

Thus, the invention provides fracture fixation devices, and methods for treating a bone fracture in a patient. The fracture fixation devices and methods improve stabilization of a bone fragment to an intramedullary nail.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A fracture fixation device comprising:
a nail section having a first end and an opposite second end, the nail section dimensioned to be positioned within an intramedullary canal of a bone such that the nail section spans a fracture site in the bone when the fracture fixation device is implanted in the bone, the nail section having a pre-insertion configuration, the nail section comprising a flexible material such that when the nail section is inserted in the intramedullary canal, the nail section bends into a post-insertion configuration different from the pre-insertion configuration and such that in bending into the post-insertion configuration wherein the entire nail section is flexible, the nail section creates frictional force at points where the nail section contacts an inner surface of the intramedullary canal; and
a nail fastening section having a first nail fastening end and an opposite second nail fastening end, the first nail fastening end being couples to the first end of the nail section, wherein at least a portion of the nail fastening section is positioned outside and extends along the bone when the fracture fixation device is implanted in the bone, and
wherein the nail section bends to extend along the nail fastening section defined between the first nail fastening end and the second nail fastening end.

2. The fracture fixation device of claim 1 wherein:
the bone has a growth plate, and
flexibility of the nail section allows the nail section to be inserted at a point in the bone that avoids disruption of the growth plate.

3. The fracture fixation device of claim 1 wherein:
the nail section bends into a generally bowed shaped when the nail section is inserted into the intramedullary canal.

4. The fracture fixation device of claim 1 wherein:
the nail fastening section includes a first throughhole for receiving a first bone screw and a second throughhole for receiving a second bone screw.

5. The fracture fixation device of claim 4 wherein:
the first throughhole is located on the first side of the fracture site when the fracture fixation device is implanted in the bone, and
the second throughhole is located on the second side of the fracture site when the fracture fixation device is implanted in the bone.

6. The fracture fixation device of claim 4 further comprising:
a first locking screw dimensioned to be inserted into the bone through the first throughhole, and
a second locking screw dimensioned to be inserted into the bone through the second throughhole.

7. The fracture fixation device of claim 4 further comprising:
a first screw dimensioned to be inserted into the bone through the first throughhole, the first throughhole being angled such that the first screw avoids the nail section when the first screw is advanced into the bone, and
a second screw dimensioned to be inserted into the bone through the second throughhole, the second throughhole being angled such that the second screw avoids the nail section when the second screw is advanced into the bone.

8. The fracture fixation device of claim 4 further comprising:
a first screw dimensioned to be inserted into the bone through the first throughhole, the first throughhole being offset from a centerline of the nail fastening section such that the first screw avoids the nail section when the first screw is advanced into the bone, and
a second screw dimensioned to be inserted into the bone through the second throughhole, the second throughhole being offset from the centerline of the nail fastening section such that the second screw avoids the nail section when the second screw is advanced into the bone.

9. The fracture fixation device of claim 1 wherein:
the connecting element comprises a tubular section of the nail fastening section, the tubular section being dimensioned to be placed over the nail section.

10. The fracture fixation device of claim 9 further comprising:
a set screw for securing the nail section in the tubular section of the nail fastening section.

11. The fracture fixation device of claim 1 wherein:
the connecting element comprises a projection of the nail fastening section, the projection being dimensioned to be placed in a cannula of the nail section.

12. The fracture fixation device of claim 1 wherein:
the nail fastening section includes a concave surface dimensioned to match a shape of an outer cortex of the bone.

13. The fracture fixation device of claim 1 wherein:
the nail fastening section includes a convex surface dimensioned to match a shape of an outer cortex of the bone.

14. The fracture fixation device of claim 1 wherein:
the nail fastening section includes a concave surface and a convex surface dimensioned to match a shape of an outer cortex of the bone.

15. The fracture fixation device of claim 1 wherein:
the nail fastening section has a serpentine shape.

16. A method for treating a bone fracture in a subject, the method comprising:
(a) providing the fracture fixation device of claim 1;
(b) positioning the nail section of the fracture fixation device within an intramedullary canal of the bone, the nail section spanning a fracture site in the bone, and a portion of the nail section being positioned outside of the intramedullary canal of the bone, when the fracture fixation device is implanted in the bone; and
(c) positioning the nail fastening section adjacent an outside surface of the bone.

17. The fracture fixation device of claim 1 wherein:
the second end of the nail section is positioned within the intramedullary canal of the bone and the first end of the nail section is positioned outside of the intramedullary canal of the bone, when the fracture fixation device is implanted in the bone.

18. The fracture fixation device of claim 1, wherein when the fracture fixation device is implanted in the bone, the second end of the nail section extends beyond the second nail fastening end.

19. A fracture fixation device comprising:
a nail section having a first end and an opposite second end, the nail section dimensioned to be positioned within an intramedullary canal of a bone such that the nail section spans a fracture site in the bone when the fracture fixation device is implanted in the bone, wherein the entire nail section is flexible; and
a separate nail fastener including a nail fastening section having a first nail fastening end and an opposite second nail fastening end, the first nail fastening end being coupled to the first end of the nail section, wherein at least a portion of the nail fastening section of the nail fastener is positioned outside and extends along the bone when the fracture fixation device is implanted in the bone, wherein the nail section bends to extend along the nail fastening section defined between the first nail fastening end and the second nail fastening end, and wherein a portion of the nail section is positioned outside of the intramedullary canal of the bone when the fracture fixation device is implanted in the bone.

20. The fracture fixation device of claim 19 wherein:
the connecting element has a tubular section dimensioned to be placed over the nail section.

21. The fracture fixation device of claim 20 further comprising:
a set screw for securing the nail section in the tubular section of the connecting element.

22. The fracture fixation device of claim 19 wherein:
the nail section has a cannula, and
the connecting element is a projection dimensioned to be inserted in the cannula when the fracture fixation device is implanted in the bone.

23. The fracture fixation device of claim 22 wherein:
the projection is dimensioned to form an interference fit when inserted in the cannula.

24. The fracture fixation device of claim 19 wherein:
the nail section is configured to bend from a pre-insertion configuration into a post-insertion configuration to contact and create a frictional force at an inner surface of the intramedullary canal of the bone, when the nail is inserted into the intramedullary canal and the fracture fixation device is implanted in the bone.

25. The fracture fixation device of claim 19 wherein:
the nail fastening section includes a first throughhole for receiving a first bone screw and a second throughhole for receiving a second bone screw.

26. The fracture fixation device of claim 25 wherein:
the first throughhole is located on a first side of the fracture site when the fracture fixation device is implanted in the bone, and
the second throughhole is located on a second side of the fracture site when the fracture fixation device is implanted in the bone.

27. The fracture fixation device of claim 26 wherein:
the nail section includes a third throughhole for receiving a third bone screw.

* * * * *

UNITED STATES PATENT AND TRADEMARK OFFICE
CERTIFICATE OF CORRECTION

PATENT NO.        : 10,543,026 B2
APPLICATION NO.   : 15/305223
DATED             : January 28, 2020
INVENTOR(S)       : Saechin Kim Page 1 of 1

It is certified that error appears in the above-identified patent and that said Letters Patent is hereby corrected as shown below:

In the Claims

Column 13, Claim 1, Line 20, "being couples to" should be --being coupled to--.

Column 16, Claim 24, Line 8, "nail is" should be --nail section is--.

Signed and Sealed this
Seventeenth Day of March, 2020

Andrei Iancu
*Director of the United States Patent and Trademark Office*